(12) United States Patent
Gunturi et al.

(10) Patent No.: US 10,736,575 B2
(45) Date of Patent: *Aug. 11, 2020

(54) ACCURACY OF HEART RATE ESTIMATION FROM PHOTOPLETHYSMOGRAPHIC (PPG) SIGNALS

(71) Applicant: Texas Instruments Incorporated, Dallas, TX (US)

(72) Inventors: Sarma Sundareswara Gunturi, Bangalore (IN); Sunil Chomal, Singapore (SG)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 80 days.

This patent is subject to a terminal disclaimer.

(21) Appl. No.: 16/166,195

(22) Filed: Oct. 22, 2018

(65) Prior Publication Data

US 2019/0053763 A1 Feb. 21, 2019

Related U.S. Application Data

(63) Continuation of application No. 15/147,720, filed on May 5, 2016, now Pat. No. 10,123,746.

(30) Foreign Application Priority Data

May 8, 2015 (IN) ............................ 2348/CHE/2015

(51) Int. Cl.
*A61B 5/00* (2006.01)
*A61B 5/024* (2006.01)

(52) U.S. Cl.
CPC .......... *A61B 5/721* (2013.01); *A61B 5/02416* (2013.01); *A61B 5/7278* (2013.01); *A61B 5/725* (2013.01); *A61B 5/7257* (2013.01); *A61B 2562/0219* (2013.01)

(58) Field of Classification Search
CPC ... A61B 5/02416; A61B 5/721; A61B 5/7214; A61B 5/725; A61B 5/7257; A61B 5/7278
USPC ........................................................ 600/479
See application file for complete search history.

(56) References Cited

U.S. PATENT DOCUMENTS

| 8,888,701 | B2 | 11/2014 | LeBouef et al. |
| 9,814,400 | B1 | 11/2017 | Cendrillon et al. |
| 9,826,940 | B1 | 11/2017 | Lengerich |
| 10,251,571 | B1 | 4/2019 | Cendrillon et al. |
| 10,602,981 | B2 | 3/2020 | Kamik et al. |
| 2006/0094943 | A1 | 5/2006 | Van Slyke |
| 2006/0122476 | A1 | 6/2006 | Van Slyke |
| 2007/0213619 | A1 | 9/2007 | Linder |
| 2008/0287815 | A1 | 11/2008 | Chon et al. |

(Continued)

*Primary Examiner* — Christopher A Flory
(74) *Attorney, Agent, or Firm* — John R. Pessetto; Charles A. Brill; Frank D. Cimino

(57) ABSTRACT

The disclosure provides a heart rate monitor (HRM) circuit. The HRM circuit includes an analog front end (AFE). The AFE receives a Photoplethysmographic (PPG) signal, and generates a fine PPG signal. A motion cancellation circuit is coupled to the AFE, and receives the fine PPG signal and an accelerometer signal. The motion cancellation circuit subtracts the accelerometer signal from the fine PPG signal to generate a coarse heart rate. A peak detector is coupled to the motion cancellation circuit and the AFE, and generates an instantaneous heart rate. A filter is coupled to the peak detector, and generates an estimated heart rate from the instantaneous heart rate, the estimated heart rate is provided as a feedback to the peak detector.

20 Claims, 6 Drawing Sheets

(56) References Cited

U.S. PATENT DOCUMENTS

| | | |
|---|---|---|
| 2010/0081946 A1 | 4/2010 | Garudadri et al. |
| 2010/0228136 A1 | 9/2010 | Keel et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0066041 A1 | 3/2011 | Pandia et al. |
| 2011/0066042 A1 | 3/2011 | Pandia et al. |
| 2011/0098583 A1 | 4/2011 | Pandia et al. |
| 2012/0197093 A1 | 8/2012 | LeBouef et al. |
| 2013/0171599 A1 | 7/2013 | Bleich et al. |
| 2013/0172760 A1 | 7/2013 | Chon et al. |
| 2013/0276785 A1 | 10/2013 | Melker et al. |
| 2014/0088385 A1 | 3/2014 | Moon et al. |
| 2014/0266939 A1 | 9/2014 | Baringer et al. |
| 2014/0273858 A1 | 9/2014 | Panther et al. |
| 2014/0275850 A1 | 9/2014 | Venkatraman et al. |
| 2014/0275852 A1 | 9/2014 | Hong et al. |
| 2014/0275854 A1 | 9/2014 | Venkatraman et al. |
| 2014/0276119 A1 | 9/2014 | Venkatraman et al. |
| 2014/0278220 A1 | 9/2014 | Yuen |
| 2014/0278229 A1 | 9/2014 | Hong et al. |
| 2014/0288390 A1 | 9/2014 | Hong et al. |
| 2014/0288391 A1 | 9/2014 | Hong et al. |
| 2014/0288392 A1 | 9/2014 | Hong et al. |
| 2014/0288435 A1 | 9/2014 | Richards et al. |
| 2014/0288436 A1 | 9/2014 | Venkatraman et al. |
| 2014/0288438 A1 | 9/2014 | Venkatraman et al. |
| 2014/0297217 A1 | 10/2014 | Yuen |
| 2014/0297218 A1 | 10/2014 | Yuen |
| 2014/0305204 A1 | 10/2014 | Hong et al. |
| 2014/0316305 A1 | 10/2014 | Venkatraman et al. |
| 2014/0358012 A1 | 12/2014 | Richards et al. |
| 2015/0025393 A1 | 1/2015 | Hong et al. |
| 2015/0025394 A1 | 1/2015 | Hong et al. |
| 2015/0031967 A1 | 1/2015 | LeBouef et al. |
| 2015/0105666 A1 | 4/2015 | Strachan |
| 2015/0122018 A1 | 5/2015 | Yuen |
| 2015/0173631 A1 | 6/2015 | Richards et al. |
| 2015/0196213 A1 | 7/2015 | Pandia et al. |
| 2015/0196256 A1 | 7/2015 | Venkatraman et al. |
| 2015/0201853 A1 | 7/2015 | Hong et al. |
| 2015/0201854 A1 | 7/2015 | Hong et al. |
| 2015/0223708 A1 | 8/2015 | Richards et al. |
| 2015/0230735 A1 | 8/2015 | Venkatraman et al. |
| 2015/0313484 A1 | 11/2015 | Burg et al. |
| 2015/0314166 A1 | 11/2015 | Hong |
| 2015/0351647 A1 | 12/2015 | Dantu et al. |
| 2016/0029898 A1 | 2/2016 | LeBouef et al. |
| 2016/0029964 A1 | 2/2016 | LeBouef et al. |
| 2016/0036118 A1 | 2/2016 | Baringer et al. |
| 2016/0038045 A1 | 2/2016 | Shapiro |
| 2016/0051157 A1 | 2/2016 | Waydo |
| 2016/0051158 A1 | 2/2016 | Silva |
| 2016/0051169 A1 | 2/2016 | Hong et al. |
| 2016/0066844 A1 | 3/2016 | Venkatraman et al. |
| 2016/0084869 A1 | 3/2016 | Yuen et al. |
| 2016/0113531 A1 | 4/2016 | Visvanathan et al. |
| 2016/0183818 A1 | 6/2016 | Richards et al. |
| 2016/0302706 A1 | 10/2016 | Richards et al. |
| 2016/0317089 A1 | 11/2016 | Fyfe et al. |
| 2016/0325143 A1 | 11/2016 | Yuen et al. |
| 2016/0361021 A1 | 12/2016 | Salehizadeh et al. |
| 2016/0374621 A1 | 12/2016 | LeBouef et al. |
| 2017/0011210 A1 | 1/2017 | Cheong et al. |
| 2017/0020398 A1 | 1/2017 | Emadzadeh |
| 2017/0027523 A1 | 2/2017 | Venkatraman et al. |
| 2017/0065184 A1 | 3/2017 | Barak |
| 2017/0084983 A1 | 3/2017 | Baringer et al. |
| 2017/0119315 A1 | 5/2017 | LeBouef et al. |
| 2017/0143272 A1 | 5/2017 | Brouse |
| 2017/0160398 A1 | 6/2017 | Venkatraman et al. |
| 2017/0188893 A1 | 7/2017 | Venkatraman et al. |
| 2017/0257162 A1 | 9/2017 | Panther et al. |
| 2018/0055450 A1 | 3/2018 | LeBouef et al. |
| 2018/0078151 A1 | 3/2018 | Allec et al. |
| 2019/0053764 A1 | 2/2019 | LeBouef et al. |

ACCURACY OF HEART RATE ESTIMATION FROM PHOTOPLETHYSMOGRAPHIC (PPG) SIGNALS

CROSS REFERENCES TO RELATED APPLICATIONS

This continuation application claims priority to U.S. patent application Ser. No. 15/147,720, filed May 5, 2016, which application claims priority from India provisional patent application No. 2348/CHE/2015, filed May 8, 2015, both applications of which are hereby incorporated herein by reference in their entirety.

TECHNICAL FIELD

The present disclosure is generally related to determining heart rate of a person, and more particularly to a heart rate monitoring circuit.

BACKGROUND

Wearable heart rate monitoring device for fitness is a fast growing market. The devices using photoplethysmograph (PPG) signals for heart rate monitoring have received significant attention in recent years. A PPG signal is an optically obtained plethysmogram, a volumetric measurement of an organ. An LED (light emitting diode) illuminates a person's skin, and a photodiode measures light absorption or reflection. The photodiode produces a PPG signal indicative of the measured light absorption or reflection. Changes in this PPG signal may be used to detect the heart rate.

The devices produce real-time estimate of heart rate from the PPG signal recorded from the wearer. A heart rate monitoring device includes a heart rate monitoring (HRM) circuit which is responsible for estimating the heart rate. However, when the person wearing the heart rate monitoring device is in motion, a motion signal strongly interferes or drowns the heart rate signal. Thus, it is important to remove the motion signal before heart rate determination.

One conventional method to separate the heart rate signal and the motion signal is to use singular spectral analysis (SSA). The PPG signal is mapped into a matrix and a singular value decomposition of the matrix is performed. The singular values and the singular vectors corresponding to the motion signal and the heart rate signal are identified and separated. The matrix corresponding to the heart rate signal is remapped to the heart rate signal for further processing. However, this method is highly complex as it requires performing matrix operations. Also, this method requires intensive computation to identify the heart rate signal as part of signal decomposition and reconstruction.

Another important requirement in a heart rate monitoring device is that, it should be of low complexity with small form factor and low power consumption as these are battery operated devices.

SUMMARY

An embodiment provides a heart rate monitoring (HRM) circuit. The HRM circuit includes an analog front end (AFE). The AFE receives a Photoplethysmographic (PPG) signal, and generates a fine PPG signal. A motion cancellation circuit is coupled to the AFE, and receives the fine PPG signal and an accelerometer signal. The motion cancellation circuit subtracts the accelerometer signal from the fine PPG signal to generate a coarse heart rate. A peak detector is coupled to the motion cancellation circuit and the AFE, and generates an instantaneous heart rate. A filter is coupled to the peak detector, and generates an estimated heart rate from the instantaneous heart rate, the estimated heart rate is provided as a feedback to the peak detector.

BRIEF DESCRIPTION OF THE VIEWS OF DRAWINGS

Figure 6:
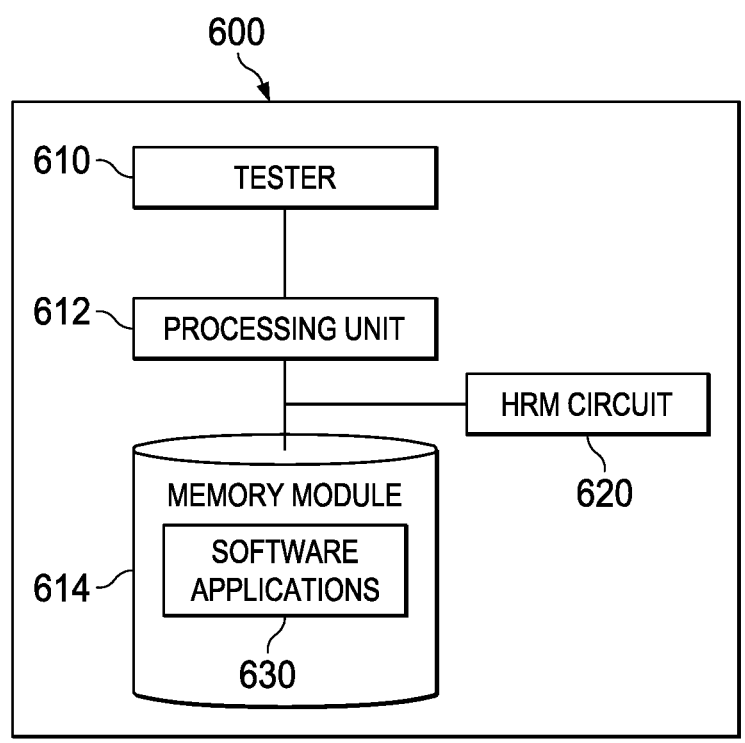
Figure 3A:
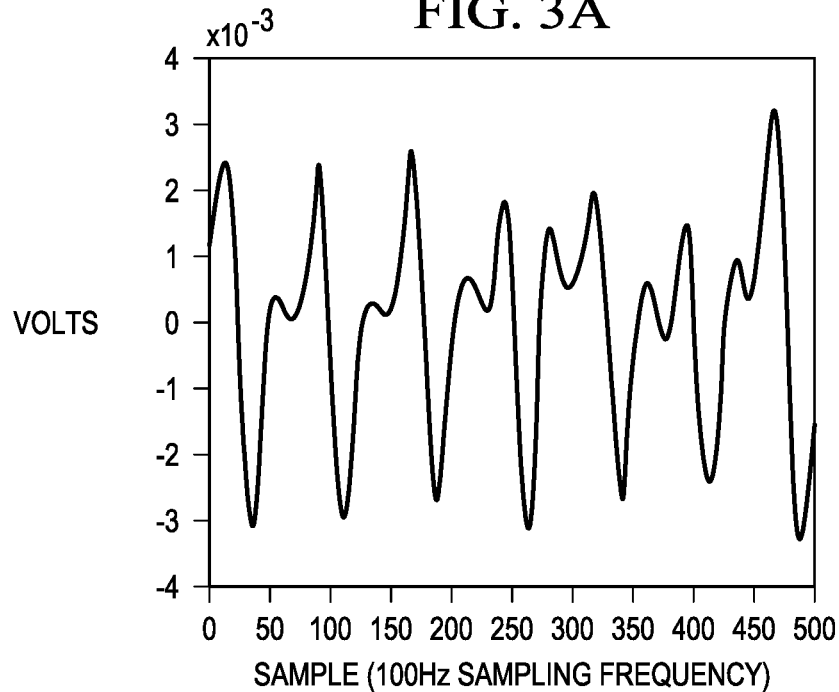
Figure 3B:
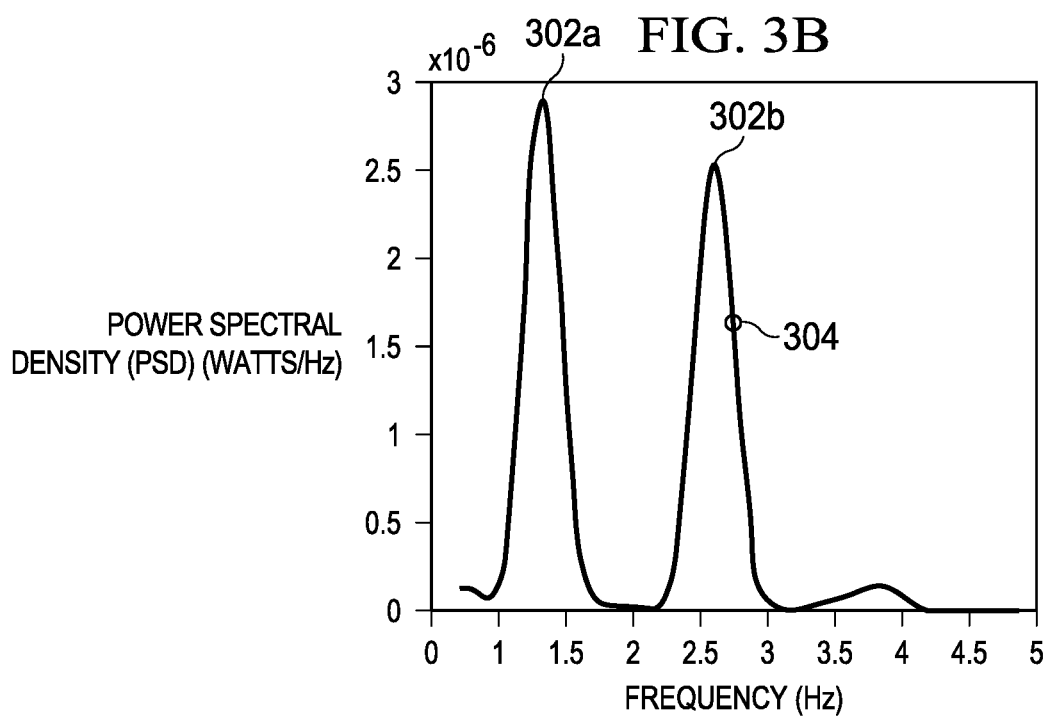
Figure 3C:
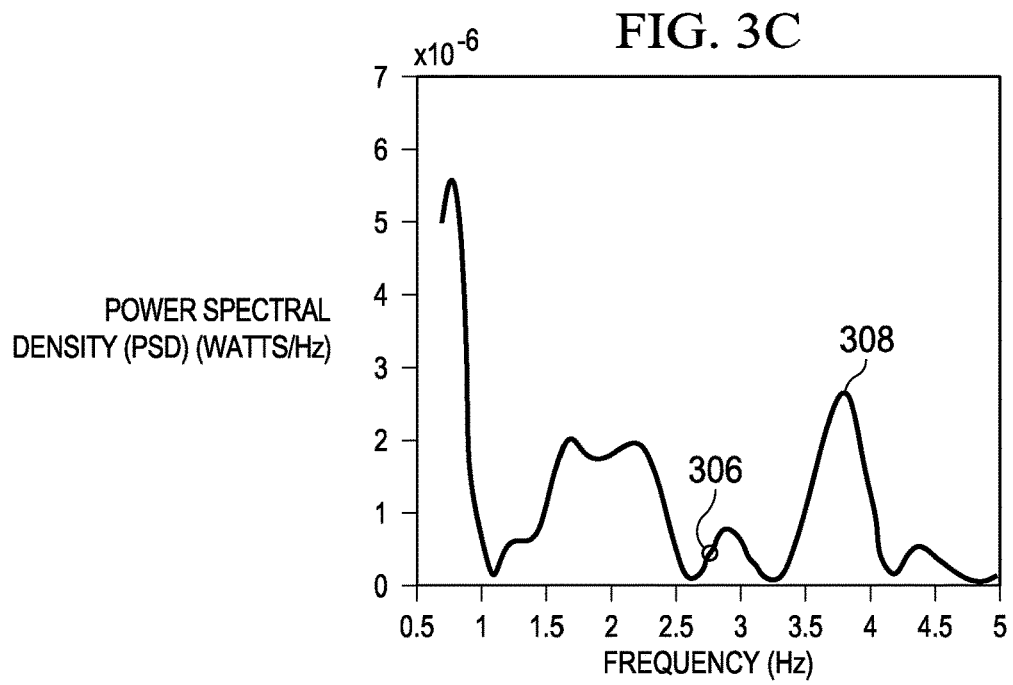
Figure 4:
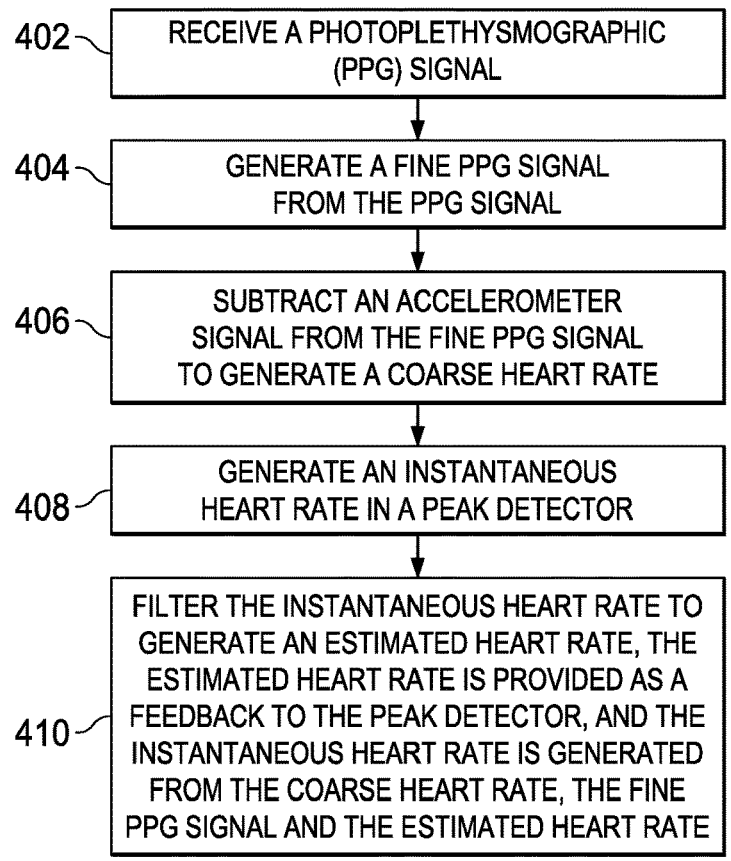
Figure 5A:
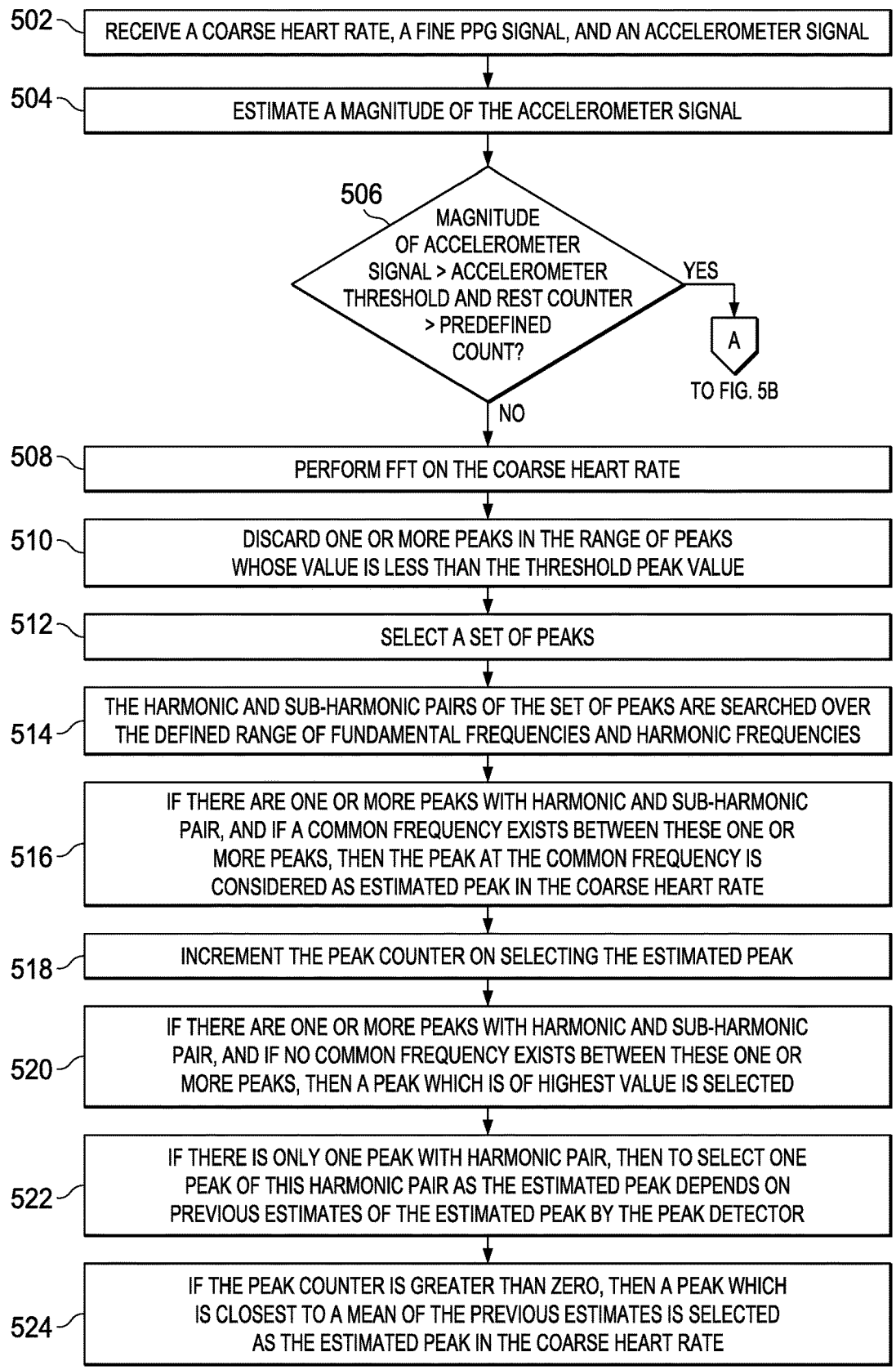
Figure 5B:
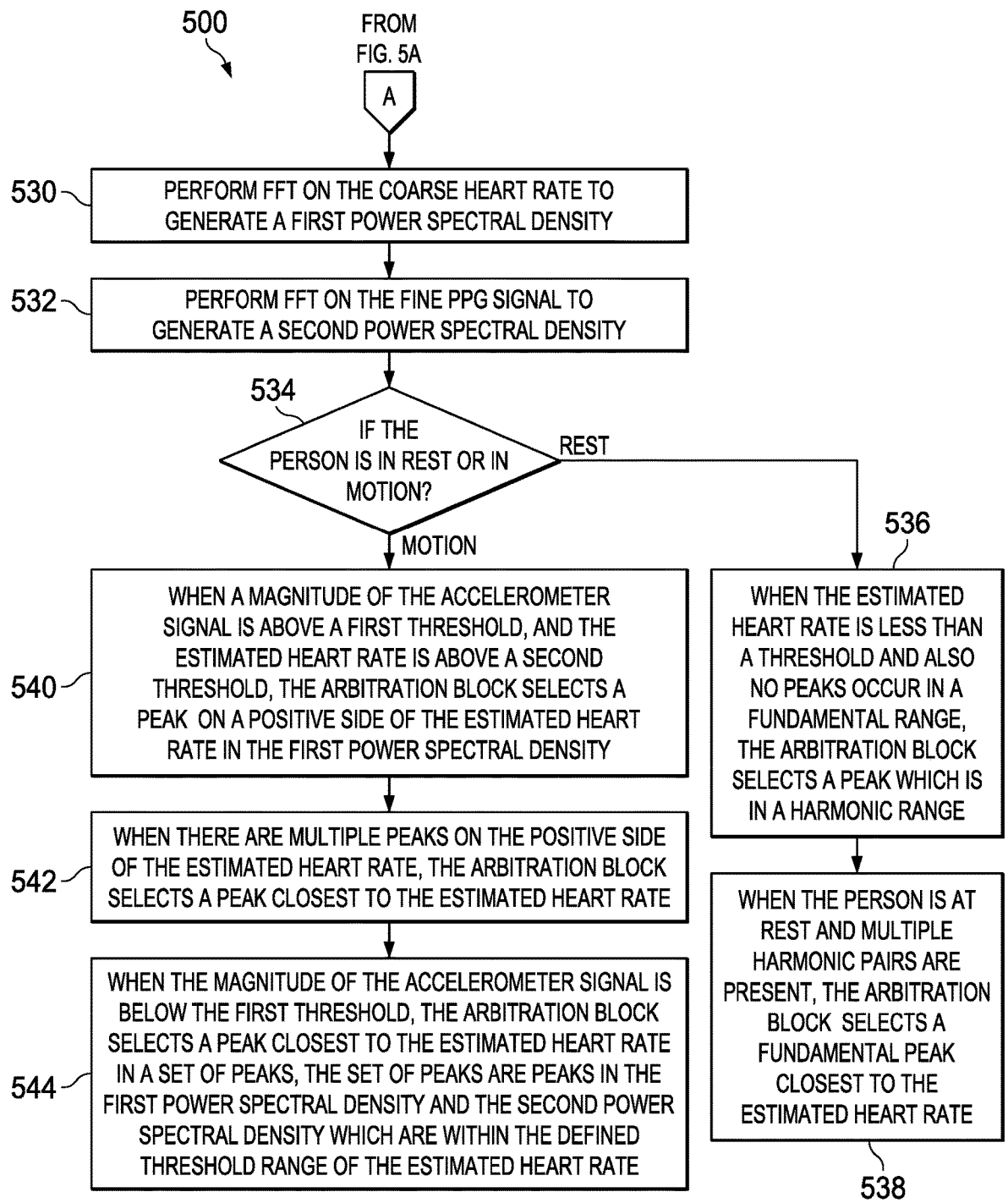

FIG. 3(A)-FIG. 3(C) illustrates operation of a heart rate monitoring (HRM) circuit, according to an embodiment;

FIG. 4 is a flowchart to illustrate a method of operation of a heart rate monitoring (HRM) circuit, according to an embodiment;

FIG. 5(A) and FIG. 5(B) provides a flowchart to illustrate a method of operation of a peak detector, according to an embodiment; and FIG. 6 illustrates a heart rate monitoring device, according to an embodiment.

DETAILED DESCRIPTION OF THE EMBODIMENTS

Figure 1:
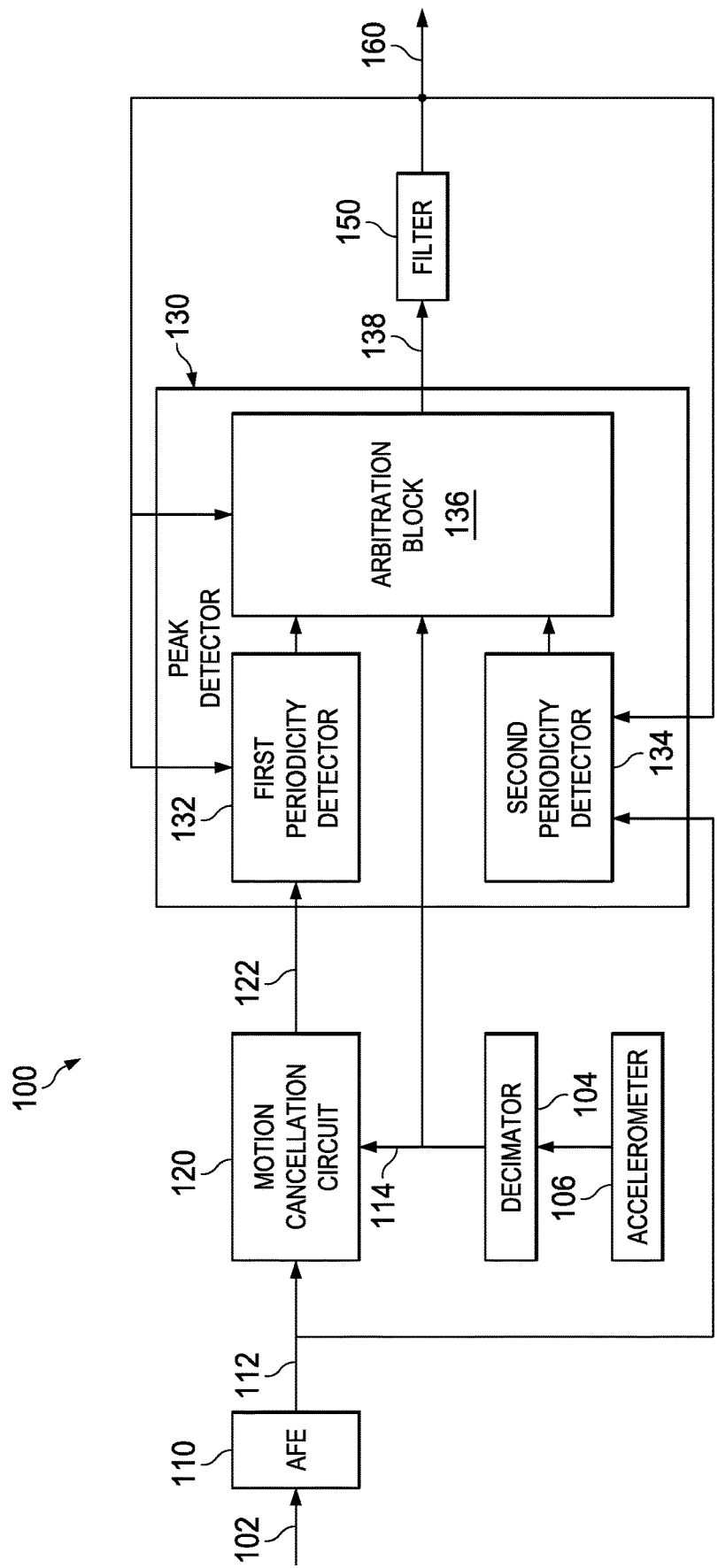
FIG. 1 illustrates a heart rate monitoring (HRM) circuit, according to an embodiment.

FIG. 1 illustrates a heart rate monitoring (HRM) circuit 100, according to an embodiment. The HRM circuit 100 includes an analog front end (AFE) 110, a decimator 104, an accelerometer 106, a motion cancellation circuit 120, a peak detector 130 and a filter 150. The AFE 110 receives a photoplethysmographic (PPG) signal 102. The accelerometer 106 is coupled to the decimator 104. The motion cancellation circuit 120 is coupled to the AFE 110 and the decimator 104.

The peak detector 130 is coupled to the motion cancellation circuit 120, the AFE 110 and the decimator 104. The peak detector 130 includes a first periodicity detector 132, a second periodicity detector 134 and an arbitration block 136. The first periodicity detector 132 is coupled to the motion cancellation circuit 120, and the second periodicity detector 134 is coupled to the AFE 110. The arbitration block 136 is coupled to the first periodicity detector 132, the second periodicity detector 134 and the decimator 104.

The filter 150 is coupled to the arbitration block 136 in the peak detector 130. The filter 150 generates an estimated heart rate 160. The estimated heart rate 160 is provided as a feedback to the first periodicity detector 132, the second periodicity detector 134 and the arbitration block 136. The HRM circuit 100 may include one or more additional components known to those skilled in the relevant art and are not discussed here for simplicity of the description.

The operation of the HRM circuit 100 illustrated in FIG. 1 is explained now. The AFE 110 receives the Photoplethysmographic (PPG) signal 102 and generates a fine PPG signal 112. The accelerometer 106 generates a coarse accelerometer signal. In one example, the coarse accelerometer signal is a representation of motion of a person wearing a heart rate monitoring (HRM) device that includes the HRM circuit 100. In another example, the accelerometer 106 is a 3-axis accelerometer.

The decimator 104 decimates the coarse accelerometer signal to generate an accelerometer signal 114. In one version, the order by which the decimator 104 decimates the coarse accelerometer signal is predefined in the HRM circuit 100. In another version, the coarse accelerometer signal is not decimated, and directly provided to the motion cancellation circuit 120.

The motion cancellation circuit 120 receives the fine PPG signal 112 and the accelerometer signal 114. The motion cancellation circuit 120 generates a coarse heart rate 122. The motion cancellation circuit 120, in one example, subtracts the accelerometer signal 114 from the fine PPG signal 112 to generate the coarse heart rate 122. In another example, the motion cancellation circuit 120 performs cancellation of the accelerometer signal 114 in a sequential manner by using motion cancellation filters.

This implies that first the x-axis motion is cancelled by a first motion cancellation filter, and an output of this forms an input for y-axis motion cancellation in a second motion cancellation filter. An output after y-axis motion cancellation forms an input for z-axis motion cancellation in a third motion cancellation filter. In one version, each motion cancellation filter is a filter whose taps are adapted to minimize a mean square error between the coarse heart rate 122 and an output of the filter. In another version, each motion cancellation filter is a filter whose taps are adapted to minimize the mean square error between an output of the previous motion cancellation filter output and the output of the filter.

The peak detector 130 receives the coarse heart rate 122, the fine PPG signal 112, the accelerometer signal 114 and the estimated heart rate 160. The peak detector 130 generates an instantaneous heart rate 138. The filter 150 generates the estimated heart rate 160 from the instantaneous heart rate 138. The filter 150, in one example, filters the instantaneous heart rate 138 to generate the estimated heart rate 160. In another example, the filter 150 is a Kalman filter. In yet another example, the filter 150 is an averaging filter.

The operation of the peak detector 130 is explained now. The first periodicity detector 132 receives the coarse heart rate 122 and the estimated heart rate 160. The second periodicity detector 134 receives the fine PPG signal 112 and the estimated heart rate 160. Each of the first periodicity detector 132 and the second periodicity detector 134 is at least one of time domain based detector and frequency domain based detector. The arbitration block 136 receives an output of the first periodicity detector 132, an output of the second periodicity detector 134 and the accelerometer signal 114. The arbitration block 136 generates the instantaneous heart rate 138.

The first periodicity detector 132 estimates peak in the coarse heart rate 122. The first periodicity detector 132 estimates a first quality metric from the estimated peak in the coarse heart rate 122 and from the estimated heart rate 160. The second periodicity detector 134 estimates peak in the fine PPG signal 112. The second periodicity detector 134 estimates a second quality metric from the estimated peak in the fine PPG signal 112 and from the estimated heart rate 160.

In one example, the first quality metric is estimated by measuring power around the estimated peak in the coarse heart rate 122. This power is termed as signal power. The remaining power in a signal generated by the first periodicity detector 132 is termed as noise power. In another example, a difference between the estimated peak in the coarse heart rate 122 and the estimated heart rate 160 is taken as the first quality metric.

The arbitration block 136 receives the estimated peak in the coarse heart rate 122 and the first quality metric from the first periodicity detector 132. The arbitration block 136 also receives the estimated peak in the fine PPG signal 112 and the second quality metric from the second periodicity detector 134. The arbitration block generates the instantaneous heart rate 138 from the estimated peak in the coarse heart rate 122, the first quality metric, the estimated peak in the fine PPG signal 112, the second quality metric, the accelerometer signal 114 and the estimated heart rate 160.

The generation of the instantaneous heart rate 138 by the peak detector 130 is further explained now. The peak detector 130 operates in an acquisition phase and a tracking phase. The acquisition phase is explained first.

In the acquisition phase, the first periodicity detector 132 performs FFT (fast Fourier transform) on the coarse heart rate 122. In one example, an FFT output is squared to generate a power spectral density. The power spectral density of the coarse heart rate 122 provides a range of peaks. The first periodicity detector 132 discards one or more peaks in the range of peaks whose value is less than a threshold peak value. The first periodicity detector 132 selects a peak which is of highest value over a defined range of fundamental frequencies and harmonic frequencies. The highest value is at least one of the highest SNR and the highest strength.

This peak is the estimated peak in the coarse heart rate 122. The first periodicity detector 132 estimates the first quality metric from the estimated peak. The first periodicity detector 132 provides the estimated peak in the coarse heart rate 122 and the first quality metric to the arbitration block 136. The estimated peak in the coarse heart rate 122 is the instantaneous heart rate 138 generated by the peak detector 130 in the acquisition phase. This instantaneous heart rate 138 is filtered by the filter 150 to generate the estimated heart rate 160.

Another approach followed during the acquisition phase is now explained. The first periodicity detector 132 performs FFT (fast Fourier transform) on the coarse heart rate 122. In one example, an FFT output is squared to generate a power spectral density. The power spectral density of the coarse heart rate 122 provides the range of peaks. The first periodicity detector 132 discards one or more peaks in the range of peaks whose value is less than the threshold peak value. The first periodicity detector 132 selects a set of peaks. The harmonic and sub-harmonic pairs of the set of peaks are searched over the defined range of fundamental frequencies and harmonic frequencies. If there are one or more peaks with harmonic and sub-harmonic pair, and if a common frequency exists between these one or more peaks, then the peak at the common frequency is considered as estimated peak in the coarse heart rate 122. A peak counter is maintained, which is incremented on selecting the estimated peak. If there are more than one common frequencies and previous estimates of the estimated peak exists, then a common frequency closest to the previous estimates is considered as the estimated peak in the coarse heart rate 122.

If there are one or more peaks with harmonic and sub-harmonic pair, and if no common frequency exists between these one or more peaks, then a peak which is of highest value is selected. The highest value is at least one of the highest SNR and the highest strength. If there is only one peak with harmonic pair, then to select one peak of this harmonic pair as the estimated peak depends on previous estimates of the estimated peak by the peak detector 130. If the peak counter is greater than zero, then a peak which is closest to a mean of the previous estimates is selected as the estimated peak in the coarse heart rate 122. If there are no previous estimates of the estimated peak, then a peak which is of highest value is selected. The highest value is at least one of the highest SNR and the highest strength.

The tracking phase is explained now. The first periodicity detector 132 performs FFT on the coarse heart rate 122 to generate a first power spectral density. The second periodicity detector 134 performs FFT on the fine PPG signal 112 to generate a second power spectral density. In one example, an FFT output is squared to generate the power spectral density. The arbitration block 136 receives the first power spectral density and the second power spectral density.

The arbitration block 136 searches peaks which are within a defined threshold range of the estimated heart rate 160. The arbitration block 136 searches peaks also based on a state of the person i.e. if the person is at rest or in motion. When the person is at rest and when the estimated heart rate 160 is less than a threshold and no peaks occur in a fundamental range and also the peaks are found in a harmonic range, then a harmonic counter is incremented. If the peaks occur in the fundamental range, then the harmonic counter is reset to zero. If the harmonic counter exceeds a predefined value then the arbitration block 136 selects a peak which is in the harmonic range. In another case, when the person is at rest and multiple harmonic pairs are present, the arbitration block 136 selects a fundamental peak closest to the estimated heart rate 160.

When the person is in motion, the arbitration block 136 uses following procedures. In a first case, when a magnitude of the accelerometer signal 114 is above a first threshold, and the estimated heart rate 160 is above a second threshold, the arbitration block 136 selects a peak on a positive side of the estimated heart rate 160 within the defined threshold range in the first power spectral density. In a second case, when there are multiple peaks on the positive side of the estimated heart rate 160 within the defined threshold range, the arbitration block 136 selects a peak closest to the estimated heart rate 160. In a third case, when the magnitude of the accelerometer signal 114 is below the first threshold, the arbitration block 136 selects peaks in the first power spectral density and the second power spectral density which are within the defined threshold range of the estimated heart rate 160 to form a set of peaks. From this set of peaks, a peak closest to the estimated heart rate 160 is selected as a new estimated heart rate.

Apart from the above cases, some other situations are discussed now. Here, in these situations, the person is in motion, and the peak detector 130 is in tracking phase. In a first situation, if no peaks are found then a peak miss counter is incremented. If the peak miss counter is above a peak miss threshold, then a search frequency range of the peak detector 130 is increased. The search frequency range of the peak detector 130 represents a frequency range on the positive and negative side of the estimated heart rate 160 within which the peaks are searched. In one example, the search frequency range around the estimated heart rate 160 is set to a new threshold.

In a second situation, if the peak miss counter is above the peak miss threshold, and a peak is found, then a new estimated heart rate is computed using this peak. A difference between the new estimated heart rate and the estimated heart rate calculated using earlier peak estimates is compared to a difference threshold. If the difference is greater than the difference threshold, then the new estimated heart rate is considered to be correct and used for further analysis. In one example, the estimated heart rate 160 is computed as a moving average of past N estimates, where N is an integer.

In a third situation, the peak detector 130 may inadvertently get locked to the accelerometer signal 114. In this situation, an FFT is performed on the accelerometer signal 114 to generate an accelerometer power spectral density in X, Y and Z axis. If a peak in the coarse heart rate 122 is within a threshold range of peaks in X, Y and Z axis, then an accelerometer flag is maintained for that peak. If the peak for which the accelerometer flag is maintained is selected as the new estimated heart rate then the peak counter is incremented. If the peak for which the accelerometer flag is maintained is not selected as the new estimated heart rate then the peak counter is reset to zero. If the peak counter exceeds a prefixed threshold then a new estimated heart rate is selected based on the previous estimated heart rate and a magnitude of the accelerometer signal.

In a fourth situation, when the peak counter is reset to zero, then the new estimated heart rate is computed using the selected peak. A difference between the new estimated heart rate and the estimated heart rate calculated using earlier peak estimates is compared to the difference threshold. If the difference is greater than the difference threshold, then the new estimated heart rate is considered to be correct and used for further analysis. In one example, the estimated heart rate is computed as a moving average of past N estimates, where N is an integer.

The HRM circuit 100 thus provides the arbitration block 136 which improves the accuracy in determining the estimated heart rate 160. The arbitration block 136 uses the previous estimated heart rate to determine the new heart rate. The use of first periodicity detector 132 and the second periodicity detector 134 provides accurate estimates to the arbitration block 136. In one example, the periodicity estimate of the fine PPG signal 112 is used to determine the periodicity estimates of the coarse heart rate 122.

The estimation of the first quality metric and the second quality metric, in one example, is based on fundamental signal level, harmonic levels, noise level and the history of the estimated heart rate 160. In one example, the first quality metric is an SNR of the estimated peak and defined as a ratio of the signal power and the noise power. In another example, the SNR of the estimated peak is used in the filter 150 to determine the estimated heart rate 160. In yet another example, the signal power is measured from a sum of power measured around the estimated fundamental peak and the harmonic peaks. The SNR of the estimated peak is used to improve an accuracy of the estimated heart rate 160 in the HRM circuit 100. The SNR of the estimated peak also helps in avoiding use of spurious peaks in the filter 150.

Figure 2:
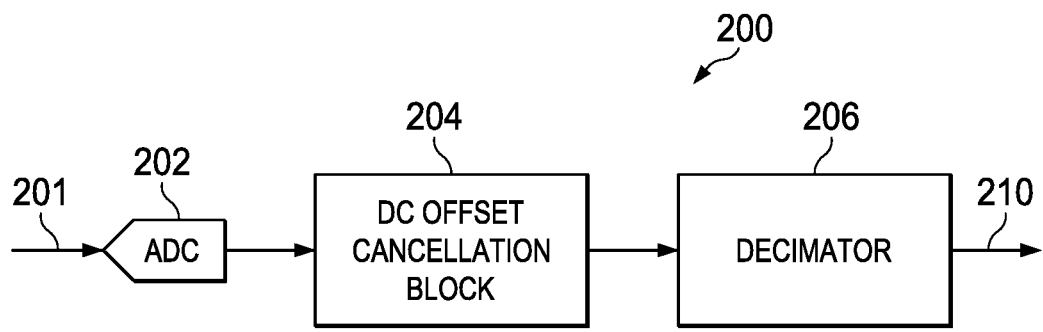
FIG. 2 illustrates an analog front end (AFE), according to an embodiment.

FIG. 2 illustrates an analog front end (AFE) 200, according to an embodiment. The AFE 200 is similar to the AFE 110 illustrated in FIG. 1 in connection and operation. The AFE 200 includes an analog to digital converter (ADC) 202, a DC offset cancellation block 204 and a decimator 206. The ADC 202 receives a photoplethysmographic (PPG) signal 201. In one version, the PPG signal 201 is generated by a photodetector (not shown), and amplified by an amplifier (not shown) before being provided to the ADC 202. The PPG signal 201 is similar to the PPG signal 102 (illustrated in FIG. 1). The DC offset cancellation block 204 is coupled to the ADC 202, and the decimator 206 is coupled to the DC offset cancellation block 204. The AFE 200 may include one or more additional components known to those skilled in the relevant art and are not discussed here for simplicity of the description.

The operation of the AFE 200 illustrated in FIG. 2 is explained now. The ADC 202 receives the PPG signal 201 and generates a digital PPG signal. The DC offset cancellation block 204 receives the digital PPG signal. The DC offset cancellation block 204 subtracts the DC offset from the digital PPG signal to generate an offset PPG signal. The decimator 206 generates a fine PPG signal 210 by decimating the offset PPG signal. The fine PPG signal 210 is similar to the fine PPG signal 112 generated by the AFE 110 in FIG. 1. In one version, the decimation of the coarse accelerometer signal is in proportion to the decimation of the offset PPG signal.

FIG. 3(a)-FIG. 3(c) illustrates operation of a heart rate monitoring (HRM) circuit, according to an embodiment. The operation is explained in connection with the HRM circuit 100 illustrated in FIG. 1. The HRM circuit receives a photoplethysmographic (PPG) signal. Also, a coarse accelerometer signal is received by the HRM circuit. The coarse accelerometer signal represents motion of a person wearing a heart rate monitoring (HRM) device that includes the HRM circuit 100.

When the person is in motion, the PPG signal includes peaks which are due to both heart rate of the person and the motion of the person. In some cases, the peaks due to motion of the person are very strong such that they completely drown the peaks due to heart rate of the person. This is represented in FIG. 3(a). FIG. 3(a) is a time domain representation of the PPG signal. The PPG signal has a periodicity which is equivalent to the motion component.

FIG. 3(b) illustrates frequency domain representation of the PPG signal. 302a and 302b represents peaks due to motion of the person. 304 represent the heart rate of the person. Thus, the peaks due to the motion of the person completely drowned the peaks due to heart rate of the person. Hence, it is important to cancel the motion component before estimating the heart rate.

The motion cancellation circuit 120 illustrated in FIG. 1 cancels the motion component from the PPG signal. However, if the peaks due to the motion of the person and due to the heart rate of the person are close to one another then the motion cancellation circuit 120 cancels the heart rate as well. Thus, the coarse heart rate 122 generated by the motion cancellation circuit 120 may not have the peaks due to the heart rate of the person. In such case, in an embodiment, the HRM circuit 100 searches for peaks in the fine PPG signal 112.

FIG. 3(c) illustrates a situation in which the heart rate is low initially i.e. the peak 306 due to heart rate is lower than peak 308 due to the motion of the person. The motion cancellation circuit 120 cancels the peak 308 due to motion of the person, and the peak detector 130 locks on to the peak 306 due to the heart rate of the person. If the motion of the person continues, the motion component may overlap the heart rate component, and in which case the motion cancellation circuit 120 highly attenuates the peak 306 due to the heart rate of the person.

In such situation, the peak detector 130 searches for peaks in the fine PPG signal 112. If the heart rate of the person continues to increase, then it might become higher than the motion component. If the peak detector 130 lock on to a peak in the fine PPG signal 112, then it may not correctly represent the heart rate of the person. In such cases, the HRM circuit 100 relies on the arbitration block 136. The arbitration block 136 follows the methodologies discussed in connection with operation of the HRM circuit 100 earlier in the instant application, and are not discussed here for brevity of the description.

FIG. 4 is a flowchart 400 to illustrate a method of operation of a heart rate monitoring (HRM) circuit, according to an embodiment. The flowchart 400 is explained in connection with the HRM circuit 100. At step 402, a Photoplethysmographic (PPG) signal is received. A fine PPG signal is generated from the PPG signal, at step 404. In the HRM circuit 100, the AFE 110 receives the PPG signal 102 and generates the fine PPG signal 112. At step 406, an accelerometer signal is subtracted from the fine PPG signal to generate a coarse heart rate. The accelerometer signal is a representation of motion of a person wearing a heart rate monitoring (HRM) device that includes the HRM circuit. In the HRM circuit 100, the motion cancellation circuit 120 subtracts the accelerometer signal 114 from the fine PPG signal 112 to generate the coarse heart rate 122.

At step 408, an instantaneous heart rate is generated in a peak detector. At step 410, the instantaneous heart rate is filtered to generate an estimated heart rate. The estimated heart rate is provided as a feedback to the peak detector, and the instantaneous heart rate is generated from the coarse heart rate, the fine PPG signal and the estimated heart rate. In the HRM circuit 100, the peak detector 130 receives the coarse heart rate 122, the fine PPG signal 112, the accelerometer signal 114 and the estimated heart rate 160. The peak detector 130 generates an instantaneous heart rate 138. The instantaneous heart rate is generated by operating the peak detector in an acquisition phase and a tracking phase which are explained in connection with FIG. 5.

FIG. 5(A) and FIG. 5(B) provides a flowchart 500 to illustrate a method of operation of a peak detector, according to an embodiment. The flowchart 500 is explained in connection with the HRM circuit 100 and the peak detector 130 illustrated in FIG. 1. At step 502, the peak detector receives a coarse heart rate, a fine PPG signal, and an accelerometer signal. The peak detector 130 receives the coarse heart rate 122, the fine PPG signal 112, the accelerometer signal 114. The accelerometer signal 114 is a representation of motion of a person wearing a heart rate monitoring (HRM) device that includes the HRM circuit 100. At step 504, a magnitude of the accelerometer signal is estimated. The magnitude of the accelerometer signal is compared with an accelerometer threshold, at step 506. When the magnitude of the accelerometer signal is above the accelerometer threshold, the person is in motion else the person is in rest. A rest counter is incremented if the person is in rest and a peak is selected. If the rest counter is lower than a predefined count, the peak detector 130 operates in an acquisition phase and proceeds to step 508. If the rest counter exceeds the predefined count, the peak detector 130 operates in a tracking phase and proceeds to step 530 (FIG. 5(B)).

At step 508, FFT is performed on the coarse heart rate. In one example, an FFT output is squared to generate the power spectral density. The power spectral density of the coarse heart rate provides the range of peaks. At step 510, one or more peaks in the range of peaks whose value is less than the threshold peak value are discarded. At step 512, a set of peaks is selected. At step 514, the harmonic and sub-harmonic pairs of the set of peaks are searched over the defined range of fundamental frequencies and harmonic frequencies. At step 516, if there are one or more peaks with harmonic and sub-harmonic pair, and if a common frequency exists between these one or more peaks, then the peak at the common frequency is considered as estimated peak in the coarse heart rate. A peak counter is maintained, which is incremented on selecting the estimated peak. If there are more than one common frequencies and previous estimates of the estimated peak exists, then a common frequency closest to the previous estimates is considered as the estimated peak in the coarse heart rate 122.

At step 520, if there are one or more peaks with harmonic and sub-harmonic pair, and if no common frequency exists between these one or more peaks, then a peak which is of highest value is selected. The highest value is at least one of the highest SNR and the highest strength. At step 522, if there is only one peak with harmonic pair, then to select one peak of this harmonic pair as the estimated peak depends on previous estimates of the estimated peak by the peak detector. If the peak counter is greater than zero, then a peak which is closest to a mean of the previous estimates is selected as the estimated peak in the coarse heart rate, at step 524. If there are no previous estimates of the estimated peak, then a peak which is of highest value is selected. The highest value is at least one of the highest SNR and the highest strength.

The tracking phase is explained now. At step 530, FFT is performed on the coarse heart rate to generate a first power spectral density. At step 532, FFT is performed on the fine PPG signal to generate a second power spectral density. In the HRM circuit 100, the first periodicity detector 132 performs FFT on the coarse heart rate 122 to generate a first power spectral density. The second periodicity detector 134 performs FFT on the fine PPG signal 112 to generate a second power spectral density. In one example, an FFT output is squared to generate the power spectral density. The arbitration block 136 receives the first power spectral density and the second power spectral density.

At step 534, a state of the person is determined. The arbitration block 136 searches peaks also based on a state of the person i.e. if the person is at rest or in motion. When the person is at rest, the system proceeds to step 536, otherwise to step 540. At step 536, when the estimated heart rate is less than a threshold and no peaks occur in a fundamental range and also the peaks are found in a harmonic range, then a harmonic counter is incremented. If the peaks occur in the fundamental range, then the harmonic counter is reset to zero. If the harmonic counter exceeds a predefined value then the arbitration block 136 selects a peak which is in a harmonic range. At step 538, when the person is at rest and multiple harmonic pairs are present, the arbitration block 136 selects a fundamental peak closest to the estimated heart rate.

When the person is in motion, the system proceeds to step 540. At step 540, when a magnitude of the accelerometer signal is above a first threshold, and the estimated heart rate is above a second threshold, the arbitration block 136 selects a peak on a positive side of the estimated heart rate within the defined threshold range in the first power spectral density. At step 542, when there are multiple peaks on the positive side of the estimated heart rate 160 within the defined threshold range then the arbitration block 136 selects a peak closest to the estimated heart rate 160. At step 543, when the magnitude of the accelerometer signal 114 is below the first threshold, the arbitration block 136 selects peaks in the first power spectral density and the second power spectral density which are within the defined threshold range of the estimated heart rate 160 to form a set of peaks. From this set of peaks, a peak closest to the estimated heart rate 160 is selected as a new estimated heart rate.

FIG. 6 illustrates a heart rate monitoring device 600, according to an embodiment. The heart rate monitoring device 600 is, or is incorporated into, a mobile communication device, such as a mobile phone, a personal digital assistant, a transceiver, a personal computer, or any other type of electronic system. The heart rate monitoring device 600 may include one or more additional components known to those skilled in the relevant art and are not discussed here for simplicity of the description.

The heart rate monitoring device 600 is placed in sufficient proximity to a person to sense the desired heart monitoring signals. For example, the heart rate monitoring device 600 may be attached to the person's skin, surgically implanted in the person's body, worn by the person (e.g., a necklace, watch, wrist band, chest band, etc.), or incorporated into exercise equipment.

In some embodiments, the heart rate monitoring device 600 comprises a megacell or a system-on-chip (SoC) which includes a processing unit 612 such as a CPU (Central Processing Unit), a memory module 614 (e.g., random access memory (RAM)) and a tester 610. The processing unit 612 can be, for example, a CISC-type (Complex Instruction Set Computer) CPU, RISC-type CPU (Reduced Instruction Set Computer), or a digital signal processor (DSP).

The memory module 614 (which can be memory such as RAM, flash memory, or disk storage) stores one or more software applications 630 (e.g., embedded applications) that, when executed by the processing unit 612, performs any suitable function associated with the heart rate monitoring device 600. The tester 610 comprises logic that supports testing and debugging of the heart rate monitoring device 600 executing the software applications 630.

For example, the tester 610 can be used to emulate a defective or unavailable component(s) of the heart rate monitoring device 600 to allow verification of how the component(s), were it actually present on the heart rate monitoring device 600, would perform in various situations (e.g., how the component(s) would interact with the software applications 630). In this way, the software applications 630 can be debugged in an environment which resembles post-production operation.

The processing unit 612 typically comprises memory and logic which store information frequently accessed from the memory module 614. The heart rate monitoring device 600 includes a heart rate monitoring (HRM) circuit 620. The HRM circuit 620 is similar in connection and operation to the HRM circuit 100. The HRM circuit 620 includes an analog front end (AFE), a decimator, an accelerometer, a motion cancellation circuit, a peak detector and a filter. The HRM circuit 620 is used to determine heart rate of the person using the heart rate monitoring device 600. The HRM circuit 620 generates an estimated heart rate which represents the heart rate of the person.

The HRM circuit 620 includes an arbitration block similar to the arbitration block 136 in the HRM circuit 100. The arbitration block improves the accuracy in determining the estimated heart rate. The arbitration block uses the previous estimated heart rate to determine the new heart rate. The use of a first periodicity detector and a second periodicity detector in the peak detector provides accurate estimates to the arbitration block.

The foregoing description sets forth numerous specific details to convey a thorough understanding of the invention. However, it will be apparent to one skilled in the art that the invention may be practiced without these specific details. Well-known features are sometimes not described in detail in order to avoid obscuring the invention. Other variations and embodiments are possible in light of above teachings, and it is thus intended that the scope of invention not be limited by this Detailed Description, but only by the following Claims.

What is claimed is:

1. A heart rate monitoring (HRM) circuit comprising:
 a peak detector configured to generate an instantaneous heart rate; and
 a filter coupled to the peak detector, and configured to generate an estimated heart rate from the instantaneous heart rate, wherein the estimated heart rate is provided as a feedback to the peak detector, and the peak detector generates the instantaneous heart rate from a coarse heart rate, a fine Photoplethysmographic (PPG) signal and the estimated heart rate.

2. The HRM circuit of claim 1 further comprising:
an analog front end (AFE) configured to receive a Photoplethysmographic (PPG) signal and configured to generate the fine PPG signal; and
a motion cancellation circuit coupled to the AFE and configured to receive the fine PPG signal and an accelerometer signal, the motion cancellation circuit configured to subtract the accelerometer signal from the fine PPG signal to generate the coarse heart rate, wherein the peak detector is coupled to the AFE and the motion cancellation circuit.

3. The HRM circuit of claim 2, wherein the peak detector comprises:
a first periodicity detector coupled to the motion cancellation circuit, and configured to receive the coarse heart rate and the estimated heart rate;
a second periodicity detector configured to receive the fine PPG signal and the estimated heart rate; and
an arbitration block coupled to the first periodicity detector and the second periodicity detector and configured to generate the instantaneous heart rate.

4. The HRM circuit of claim 3, wherein the estimated heart rate is provided as feedback to the first periodicity detector, the second periodicity detector and the arbitration block.

5. The HRM circuit of claim 2, wherein the AFE comprises:
an analog to digital converter (ADC) configured to receive the PPG signal, the ADC configured to generate a digital PPG signal from the PPG signal;
a DC offset cancellation block configured to subtract DC offset from the digital PPG signal to generate an offset PPG signal; and
a decimator configured to decimate the offset PPG signal to generate the fine PPG signal.

6. The HRM circuit of claim 3, wherein the first periodicity detector is configured to estimate peak in the coarse heart rate, and the second periodicity detector is configured to estimate peak in the fine PPG signal.

7. The HRM circuit of claim 6, wherein:
the first periodicity detector is configured to estimate a first quality metric from the estimated peak in the coarse heart rate and from the estimated heart rate; and
the second periodicity detector is configured to estimate a second quality metric from the estimated peak in the fine PPG signal and from the estimated heart rate.

8. The HRM circuit of claim 7, wherein the arbitration block is configured to generate the instantaneous heart rate from the estimated peak in the coarse heart rate, the estimated peak in the fine PPG signal, the first quality metric, the second quality metric, the accelerometer signal and the estimated heart rate.

9. A method for monitoring heart rate of a person comprising:
generating an instantaneous heart rate in a peak detector; and
filtering the instantaneous heart rate to generate an estimated heart rate, wherein the estimated heart rate is provided as a feedback to the peak detector, and the instantaneous heart rate is generated from a coarse heart rate, a fine Photoplethysmographic (PPG) signal and the estimated heart rate.

10. The method of claim 9 further comprising:
receiving a Photoplethysmographic (PPG) signal;
generating the fine PPG signal from the PPG signal; and
subtracting an accelerometer signal from the fine PPG signal to generate the coarse heart rate.

11. The method of claim 10, wherein generating the fine PPG signal from the PPG signal further comprises:
generating a digital PPG signal from the PPG signal;
subtracting DC offset from the digital PPG signal to generate an offset PPG signal; and
decimating the offset PPG signal to generate the fine PPG signal.

12. The method of claim 11 further comprising decimating a coarse accelerometer signal in proportion to the decimation of the offset PPG signal to generate the accelerometer signal.

13. The method of claim 9, wherein generating the instantaneous heart rate further comprises operating the peak detector in an acquisition phase and a tracking phase.

14. The method of claim 13, wherein in the acquisition phase:
performing FFT on the coarse heart rate to estimate a range of peaks in the coarse heart rate;
discarding one or more peaks whose value is less than a threshold peak value;
selecting an estimated peak which is of a highest value over a defined range of fundamental frequencies and harmonic frequencies, the estimated peak is the instantaneous heart rate generated by the peak detector; and
estimating a first quality metric from the estimated peak.

15. The method of claim 13, wherein in the tracking phase:
performing FFT on the coarse heart rate to generate a first power spectral density;
performing FFT on the fine PPG signal to generate a second power spectral density; and
searching peaks which are within a defined threshold range of the estimated heart rate and based on a state of the person, the state of the person includes a person at rest and a person in motion.

16. The method of claim 15, wherein searching peaks when the person is at rest further comprises:
selecting a peak in a harmonic range when the estimated heart rate is less than a threshold and no peaks occur in a fundamental range; and
selecting a fundamental peak closest to the estimated heart rate when multiple harmonic pairs are present.

17. The method of claim 15, wherein searching peaks when the person is in motion further comprises:
selecting a peak on a positive side of the estimated heart rate in the first power spectral density when a magnitude of the accelerometer signal is above a first threshold, and the estimated heart rate is above a second threshold;
selecting a peak closest to the estimated heart rate when multiple peaks are present on the positive side of the estimated heart rate; and
selecting a peak closest to the estimated heart rate in a set of peaks when the magnitude of the accelerometer signal is below the first threshold, the set of peaks are peaks in the first power spectral density and the second power spectral density which are within the defined threshold range of the estimated heart rate.

18. A device comprising:
a processing unit; and
a heart rate monitoring (HRM) circuit coupled to the processing unit, the HRM circuit comprising:

a peak detector configured to generate an instantaneous heart rate; and a filter coupled to the peak detector, and configured to generate an estimated heart rate from the instantaneous heart rate, wherein the estimated heart rate is provided as a feedback to the peak detector, and the peak detector generates the instantaneous heart rate from a coarse heart rate, a fine Photoplethysmographic (PPG) signal and the estimated heart rate.

19. The device of claim 18, wherein the HRM circuit further comprises:

an analog front end (AFE) configured to receive a Photoplethysmographic (PPG) signal and configured to generate the fine PPG signal; and a motion cancellation circuit coupled to the AFE and configured to receive the fine PPG signal and an accelerometer signal, the motion cancellation circuit configured to subtract the accelerometer signal from the fine PPG signal to generate the coarse heart rate, the peak detector is coupled to the AFE and the motion cancellation circuit.

20. The device of claim 19, wherein the peak detector further comprises:

a first periodicity detector coupled to the motion cancellation circuit, and configured to receive the coarse heart rate and the estimated heart rate;

a second periodicity detector configured to receive the fine PPG signal and the estimated heart rate; and an arbitration block coupled to the first periodicity detector and the second periodicity detector and configured to generate the instantaneous heart rate, wherein the estimated heart rate is provided as feedback to the first periodicity detector, the second periodicity detector and the arbitration block.

* * * * *